United States Patent
Moriyama et al.

(10) Patent No.: US 7,276,343 B2
(45) Date of Patent: Oct. 2, 2007

(54) CHEMILUMINESCENCE ENHANCER

(75) Inventors: Kazushige Moriyama, Tokyo (JP); Tetsuji Tanimoto, Tokyo (JP); Tatsuki Matsuno, Tokyo (JP); Yoshihiro Ashihara, Tokyo (JP)

(73) Assignee: Fujirebio Inc., Tokyo (JP)

( * ) Notice: Subject to any disclaimer, the term of this patent is extended or adjusted under 35 U.S.C. 154(b) by 0 days.

(21) Appl. No.: 10/518,586

(22) PCT Filed: Jun. 24, 2003

(86) PCT No.: PCT/JP03/07985

§ 371 (c)(1),
(2), (4) Date: Dec. 21, 2004

(87) PCT Pub. No.: WO04/001415

PCT Pub. Date: Dec. 31, 2003

(65) Prior Publication Data

US 2005/0239149 A1 Oct. 27, 2005

(30) Foreign Application Priority Data

Jun. 24, 2002 (JP) .............................. 2002-183720

(51) Int. Cl.
| | |
|---|---|
| *G01N 33/53* | (2006.01) |
| *G01N 33/542* | (2006.01) |
| *G01N 33/543* | (2006.01) |
| *G01N 33/553* | (2006.01) |
| *G01N 33/566* | (2006.01) |
| *G01N 21/75* | (2006.01) |
| *G01N 21/76* | (2006.01) |
| *C12Q 1/00* | (2006.01) |
| *C12N 9/00* | (2006.01) |
| *C09K 3/00* | (2006.01) |

(52) U.S. Cl. .............................. 435/7.1; 435/4; 435/7.9; 435/183; 436/164; 436/172; 436/501; 436/518; 436/526; 252/700

(58) Field of Classification Search .................. 435/4, 435/7.1, 183, 7.9; 436/501, 164, 172, 518, 436/526; 252/700
See application file for complete search history.

(56) References Cited

U.S. PATENT DOCUMENTS

| | | | | | |
|---|---|---|---|---|---|
| 3,704,231 | A | * | 11/1972 | Bollyky ....................... | 252/700 |
| 5,094,939 | A | * | 3/1992 | Okada et al. ................. | 435/6 |
| 5,112,960 | A | * | 5/1992 | Bronstein et al. .......... | 536/18.1 |
| 5,753,436 | A | * | 5/1998 | Bronstein et al. ............. | 435/6 |
| 6,045,727 | A | * | 4/2000 | Akhavan-Tafti et al. .... | 252/700 |
| 6,124,109 | A | * | 9/2000 | El Alaoui et al. .......... | 435/7.92 |
| 2002/0019553 | A1 | * | 2/2002 | Akhavan-Tafti et al. .... | 558/167 |
| 2002/0164271 | A1 | * | 11/2002 | Ho .......................... | 422/82.08 |

FOREIGN PATENT DOCUMENTS

| | | | |
|---|---|---|---|
| GB | 2233451 A | * | 9/1991 |
| JP | 2-273200 | | 11/1990 |
| JP | 3-53897 | | 3/1991 |
| JP | 9-507571 | | 7/1997 |

\* cited by examiner

*Primary Examiner*—Long V. Le
*Assistant Examiner*—Jacqueline A. DiRamio
(74) *Attorney, Agent, or Firm*—Oblon, Spivak, McClelland, Maier & Neustadt, P.C.

(57) ABSTRACT

The present invention provides a chemiluminescence enhancer treated to retain favorable dispersibility of fine solid carriers and stably exert a chemiluminescence enhancing action. The invention provides a chemiluminescence enhancer used for signal detection in a solid phase immunoassay using antigen or/and antibody immobilized onto fine solid carriers dispersible in a liquid medium, consisting of a water soluble macromolecular quaternary ammonium salt, a quaternary sulfonium salt or a quaternary phosphonium salt in order to enhance emission of light caused by an enzymatic reaction of a chemiluminescent substrate having dioxetane, wherein the chemiluminescence enhancer is given an aggregation inhibition treatment of the fine solid carriers by the treatment with an oxidizing agent or a reducing agent, and a chemiluminescence method and a kit using the chemiluminescence enhancer.

11 Claims, No Drawings

CHEMILUMINESCENCE ENHANCER

TECHNICAL FIELD

The present invention relates to a chemiluminescence enhancer used for enhancing chemiluminescence which is caused by enzymatic action of a chemiluminescent substrate in signal detection in a solid phase immunoassay using antigen or/and antibody immobilized onto fine solid carriers dispersible in a liquid medium.

BACKGROUND ART

In the field of measuring trace components, particularly in the field of clinical diagnostics, measurement methods of applying principles of immunology are utilized and immunoassays using fine solid carriers as a solid phase are widely used. The fine solid carriers include erythrocytes, gelatin particles, latex particles and the like, and a quantitative analysis is performed by absorbing antigen or/and antibody on the surface thereof and reacting immunologically the antibody or/and the antigen against antigen or/and antibody in a test sample. It is well-known that the immunoassays using these fine solid carriers are also commonly used even in the fields other than clinical diagnosis.

Chemiluminescence measurement utilizing chemiluminescence reaction in which the chemiluminescence is caused by allowing an enzyme such as alkaline phosphatase to act upon a chemiluminescent substrate such as 1,2-dioxetanes can rapidly and sensitively measure the presence or concentration of a measurement subject in a specimen, and has been widely used to measure viruses such as HIV and HCV, and other trace components in vivo (JP 96-507694).

It is well-known that a quenching reaction occurs in a liquid medium, particularly in an aqueous medium with chemiluminescence by decomposition of chemiluminescent substrate having dioxetane. Many test samples are biological samples in general, and thus the measurement of the samples by such a method is generally performed in an aqueous medium. Therefore, the quenching reaction sometimes reduces substantially the chemiluminescence occurred by the decomposition of the chemiluminescent substrate having dioxetane, which is actually obsereved. In the measurement methods of certain test samples, e.g., nucleic acids, a viral antibody and other proteins, in which a detection at a low level is required, the chemiluminescence reduced by the quenching reaction in combination with unavoidable background signals reduces the sensitivity of the measurement method, and thus in some cases, those at an extremely low level can not be detected. In order to improve these quenching reactions, an addition of a water soluble macromolecule including both naturally occurring and synthetic molecules (see U.S. Pat. No. 5,145,722), an addition of various water soluble enhancers to test samples (see U.S. Pat. No. 4,978,614), or water soluble polymerized quaternary ammonium salts such as poly(vinylbenzyltrimethyl ammonium chloride) (TMQ), poly(vinylbenzyltributyl ammonium chloride) (TBQ) and poly(vinylbenzyldimethylbenzyl ammonium chloride) (BDMQ) as the water soluble polymerized quaternary ammonium salts has been used (see U.S. Pat. No. 5,112,960 and JP 8-507694 T).

In the meanwhile, the chemiluminescence enhancers such as TMQ, TBQ and BDMQ described above are polymers with high molecular weight. In the case of being used for a signal detection in a solid phase immunoassay using antigen or/and antibody immobilized onto a fine solid carrier dispersible in a liquid medium, when the carriers are once physically aggregated, for example, in order to wash after an immune reaction, these polymers prevent the fine solid carriers from dispersing thereafter, inhibit luminescence caused by an enzymatic reaction of the chemiluminescent substrate having dioxetane depending on the concentration of the subject substance to be detected, and have sometimes had a problem in that no precise measurement value can be obtained.

DISCLOSURE OF THE INVENTION

The aim of the invention is to provide a chemiluminescence enhancer made by treating a known chemiluminescence enhancer to retain favorable dispersibility of fine solid carriers in a chemiluminescence reaction by a chemiluminescent substrate and stably exert a chemiluminescence enhancing action.

As a result of intensive study, the inventors of the present invention have found that a chemiluminescence enhancer such as water soluble macromolecular quaternary ammonium salt, quaternary sulfonium salt (sulfonium salt) or quaternary phosphonium salt treated with a reagent having an oxidation or reduction property more stably enhances emission of light caused by an enzymatic reaction of a chemiluminescent substrate having dioxetane in signal detection in a solid phase immunoassay and provides more precise measurement results, and have completed the invention.

That is, the invention provides a chemiluminescence enhancer used for signal detection in a solid phase immunoassay using antigen or/and antibody immobilized onto fine solid carriers dispersible in a liquid medium, consisting of a water soluble macromolecular quaternary ammonium salt, a quaternary sulfonium salt or a quaternary phosphonium salt in order to enhance emission of light caused by an enzymatic reaction of a chemiluminescent substrate having dioxetane, wherein the chemiluminescence enhancer is given an aggregation inhibition treatment of the fine solid carriers by the treatment with an oxidizing agent or a reducing agent, and a chemiluminescence method and a kit using the chemiluminescence enhancer.

A preferable aspect of the enhancer is the chemiluminescence enhancer which does not substantially contain a component of a molecular weight more than about 400,000 daltons in the molecular weight separated by an ultrafiltration method.

BEST MODE FOR CARRYING OUT THE INVENTION

As described above, the chemiluminescence enhancer of the invention is water soluble macromolecular quaternary ammonium salt, quaternary sulfonium salt or quaternary phosphonium salt, or the like which is treated with a reagent having oxidation or reduction property, and is represented by following general formula (I):

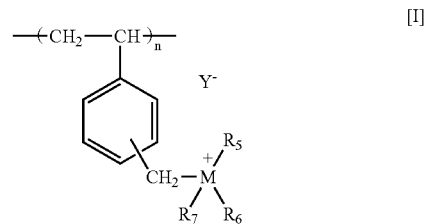

In general formula (I), each of $R_5$, $R_6$ and $R_7$ may be a straight or branched, unsubstituted alkyl group having 1 to 20 carbon atoms (e.g., methyl group, ethyl group, n-butyl group, t-butyl group or hexyl group or the like); a straight or branched alkyl group having 1 to 20 carbon atoms substituted with one or more of a hydroxyl group, an alkoxy group (e.g., methoxy, ethoxy, benzyloxy or polyoxyethylethoxy group), an aryloxy group (e.g., phenoxy group), an amino group, a substituted amino group (e.g., methylamino), an amide group (e.g., acetamide group) or an ureide group (e.g., phenylureide group); a fluoroalkane group; a fluoroaryl group (e.g., heptafluorobutyl group); an unsubstituted monocycloalkyl group having 3 to 12 ring carbon atoms (e.g., cyclohexyl or cyclooctyl group); a substituted monocycloalkyl group having 3 to 12 ring carbon atoms substituted with one or more of an alkyl group, an alkoxy group or a condensed benzo group (e.g., methoxycyclohexyl or 1,2,3,4-tetrahydronaphthyl group); polycycloalkyl group having two or more condensed rings each having 5 to 12 carbon atoms, which is unsubstituted or substituted with one or more of an alkyl group, an alkoxy group or an aryl group (e.g., 1-adamantyl or 3-phenyl-1-adamantyl group); an aryl group, an alkaryl group or an aralkyl group having at least one ring and totally 6 to 20 carbon atoms, which is unsubstituted or substituted with one or more of an alkyl group, an aryl group, fluorine or a hydroxyl group (e.g., phenyl, naphthyl, pentafluorophenyl, ethylphenyl, benzyl, hydroxybenzyl, phenylbenzyl or dehydroabiethyl group). At least two of $R_5$, $R_6$ and $R_7$ mean the groups capable of forming together with a quaternary atom to which they are bound a saturated or unsaturated, unsubstituted or substituted ring having 3 to 5 carbon atoms and 1 to 3 heteroatoms and containing nitrogen, phosphorus or sulfur, to which a benzene ring may be condensed (e.g., 1-pyridinium, 1-(3-alkyl) imidazolium, 1-(3-aralkyl)imidazolium, morpholino, alkyl morpholinium, alkyl piperidinium, N-acyl piperidinium, piperidino, acyl piperidino, benzoxazolium, benzothiazolium or benzamidazolium).

A symbol Y in the general formula [I] alone or in combination represents a counter ion capable of including moieties such as a halogen ion, i.e., fluorine ion, chlorine ion, bromine ion and iodine ion, sulfate ion, alkyl sulfonate ion (e.g., methyl sulfonate ion), aryl sulfonate ion (e.g., p-toluene sulfonate ion), substituted aryl sulfonate ion (e.g., anilinonaphthylene sulfonate ion and various isomers thereof), diphenylantracene sulfonate ion, perchlorate ion, alkanoate ion (e.g., acetate ion), aryl carboxylate ion (e.g., fluorescein or fluorescein derivatives), benzene heterocyclic aryl carboxylate ion (e.g., 7-diethylamino-4-cyanocoumarin-3-carboxylate ion). Organic dianions such as p-terephthalate ion may be represented by Y.

Furthermore, a symbol n represents a number over the range of about 500 to about 500,000 (average molecular weight), preferably about 20,000 to about 70,000 when the molecular weight of such poly(vinylbenzyl quaternary salt) is measured using an intrinsic viscosity or an LALLS method. Methods of preparing these polymers where M is nitrogen, related copolymers and related starting materials are disclosed in Jones, G. D., Journal of Polymer Science, Vol. 25:201, 1958; U.S. Pat. No. 2,780,604, U.S. Pat. No. 3,178,396, U.S. Pat. No. 3,770,439, U.S. Pat. No. 4,308,335, U.S. Pat. No. 4,340,522, U.S. Pat. No. 4,424,326 and German published Patent No. 2,447, 611. A symbol M may be phosphorus or sulfur, and here, corresponding phosphonium or sulfonium polymers are described in prior art (U.S. Pat. No. 3,236,820 and U.S. Pat. No. 3,065,272).

As the chemiluminescence enhancer having the structure denoted by the general formula [I], those selected from poly[vinylbenzyl(benzylmethyl ammonium chloride)] (BDMQ), poly(vinylbenzyltrimethyl ammonium chloride) (TMQ), poly[vinylbenzyl(tributyl ammonium chloride)] (TBQ), benzylmethylcetyl ammonium chloride (BDM-CAC), polymethacrylamidepropylenemethyl ammonium chloride (poly MAPTAC), poly[vinylbenzyl(triethyl ammonium chloride)] (TEQ), poly[vinylbenzyl(2-benzylamino) ethyldimethyl ammonium chloride] (BAEDM), poly[vinylbenzyldimethyl(2-hydroxy)ethyl ammonium chloride] (DME(OH)B), poly[vinylbenzyl(trimethylphosphonium chloride)] (TM), poly[vinylbenzyl(tributylphosphonium chloride)] (TB) and poly[vinylbenzyl(trioctylphosphonium chloride)] (TO) and copolymers thereof are suitable.

The chemiluminescence enhancers of general formula [I] which is particularly preferable in the invention are those selected from poly[vinylbenzyl(benzylmethyl ammonium chloride)] (BDMQ), poly(vinylbenzyltrimethyl ammonium chloride) (TMQ), poly[vinylbenzyl(tributyl ammonium chloride)] (TBQ), poly[vinylbenzyl(triethyl ammonium chloride)] (TEQ), poly[vinylbenzyl (trimethylphosphonium chloride)] (TM), poly[vinylbenzyl(tributylphosphonium chloride)] (TB) and poly[vinylbenzyl(trioctylphosphonium chloride)] (TO) and copolymers thereof, more preferably those selected from poly(vinylbenzyltrimethyl ammonium chloride) (TMQ), poly[vinylbenzyl(tributyl ammonium chloride)] (TBQ) and poly[vinylbenzyl(benzylmethyl ammonium chloride)] (BDMQ), poly[vinylbenzyl(triethyl ammonium chloride)] (TEQ), and copolymers thereof, and most preferably poly[vinylbenzyl(tributyl ammonium chloride)] (TBQ) and poly[vinylbenzyl(benzylmethyl ammonium chloride)] (BDMQ).

As described in the following general formula [II], a copolymer having two or more different onium side chains can be also utilized in the invention set forth here. The symbols Y, M', $R_5'$, $R_6'$ and $R_7'$ are the same as defined above Y, M, $R_5$, $R_6$ and $R_7$. The symbols y and z represent a molar fraction of an individual monomer which constitutes the copolymer. Therefore, a sum of the symbols y and z is always equal to 1, and each of them may vary from 0.01 to 0.99. As a suitable moiety, M is nitrogen or phosphorus, and $R_5$ to $R_7$ are each independently an alkyl, cycloalkyl, polycycloalkyl (e.g., adamantane group), aralkyl or aryl group having 1 to 20 carbon atoms unsubstituted or further substituted with a hydroxyl, amino, amide or ureide group, or together form a heterocyclic (in some cases, aromatic or aliphatic or mixed including other heteroatoms such as nitrogen, sulfur or oxygen) onium group via a spiro-bond with an M atom.

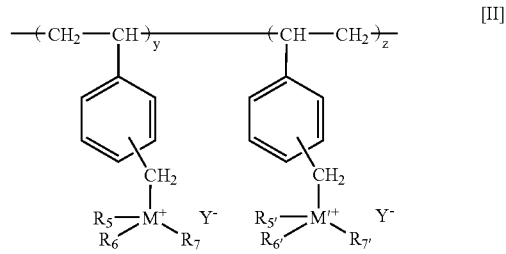

The chemiluminescence reaction itself in which the chemiluminescence enhancer of the invention is used is known. Enzymes for performing the chemiluminescence reaction can include acid phosphatase, alkali phosphatase, galactosidase, glucosidase, glucuronidase or esterase, and preferable examples can include acid phosphatase, alkali phosphatase, glucosidase, galactosidase and esterase. The most preferable is alkali phosphatase. These enzymes can be purified from animals, plants, bacteria and the like by methods known publicly, and are also commercially available. Commercially available articles can be also preferably used. These enzymes may be in a free state or in a state bound to the other substance such as an antigen, an antibody and a hapten.

The substrate of the chemiluminescence reaction used here can include a dioxetane derivative represented by the following general formula [III]:

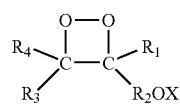

wherein $R_2$ is an aryl group substituted with an X-oxy group, which forms 1,2-dioxetane compound which is an unstable oxide intermediate when X is eliminated by an activator selected from acid, base, salt, enzyme, organic or inorganic catalyst and electron donor to induce a reaction, and the unstable 1,2-dioxetane compound is decomposed with releasing electron energy to produce light and two carbonyl containing compounds, further, X is a chemically easily reactive group which is eliminated by an enzyme; $R_1$ is selected from the group consisting of an alkyl group, alkoxy group, aryloxy group, dialkylamino group, trialkylsilyloxy group, arylsilyloxy group, aryl group, and an aryl group which forms a polycyclic aryl group of X-oxy substituent spiro-bound to a 1,2-dioxetane ring by binding to an aryl group $R_2$; $R_3$ and $R_4$ are each an alkyl or heteroalkyl group and $R_3$ and $R_4$ may be bound one another to form a polycyclic alkylene group spiro-bound to the 1,2-dioxetane ring.

In general formula [III], when $R_1$ is not bound to $R_2$, this $R_1$ is an alkyl, alkoxy, aryloxy, dialkylamino, trialkylsilyloxy, arylsilyloxy or aryl group as described above, and preferably a lower alkyl or alkoxy group having 1 to 8 carbon atoms. $R_1$ may be also an aryl, aryloxy or arylsilyloxy group having 6 to 20 carbon atoms. When $R_1$ is bound to $R_2$ which is an aryl group to form a polycyclic aryl group spiro-bound to the 1,2-dioxetane ring, it is preferable that the polycyclic aryl group has carbon atoms up to 30. The polycyclic aryl group in this case may be one where an oxygen atom is included in place of a carbon atom as a xanthenyl group, and fluorenyl or xanthenyl where the spiro-bound polycyclic aryl group is spiro-bound to the 1,2-dioxetane ring at position C9 of the group is preferable.

$R_2$ is an aryl group substituted with X-oxy group (OX group), and the group including the aryl group may be a phenyl, biphenyl, bound phenyl group or other aryl group, include 6 to 30 carbon atoms, and include another substituent. X is a group eliminated from dioxetane by the activator in order to decompose a stable dioxetane structure to produce chemiluminescence (signal). It is preferred that the OX group is selected from a hydroxyl, alkylsilyloxy, arylsilyloxy group, an inorganic oxy acid salt (particularly, phosphate salt or sulfate salt), pyranoside oxygen, an arylcarboxylester or alkylcarboxylester group. When the OX group is a hydroxy group, a hydrogen atom of the group is easily reactive with an organic base such as potassium t-butoxide or an inorganic base such as potassium hydroxide, and can be decomposed by the base to produce the chemiluminescence. When the activator is an enzyme typically frequently used as a label for an immunoassay or a detection of a DNA probe, the OX group having X which is easily reactive with the enzyme could be appropriately selected. For example, when the activator is alkali phosphatase, β-galactosidase, aryl or acetylcholine esterase, or the like commonly used as one detected by a colorimetric substrate or a fluorescent substrate in the immunoassay or the detection of the DNA probe, a phosphate salt, pyranoside oxygen or an acetate ester group can be selected as the OX group.

$R_3$ or $R_4$ is each an alkyl group or a heteroalkyl group, and may be bound one another to form a ring structure and make a polycyclic alkylene group. The polycyclic alkylene group may include 6 to 30 carbon atoms, and include heteroatoms (nitrogen, oxygen, sulfur or phosphorus). The preferable polycyclic alkylene group is an adamantyl group. $R_3$ and $R_4$ bring stability to the dioxetane structure, and may have a substituent so long as the substituent does not impair the stability.

In the compounds having the dioxetane structure as in the above, the suitable chemiluminescent substrates are 3-(4-methoxyspiro[1,2-dioxetane-3,2'-tricyclo[3.3.1$^{3.7}$]decane]-4-yl)phenyl phosphoric acid and particularly disodium salt thereof (AMPPD), and 3-(4-methoxyspiro[1,2-dioxetane-3, 2'-(5'-chloro)tricyclo[3.3.1$^{3.7}$]decane]-4-yl)phenyl phosphoric acid and particularly disodium salt thereof (CSPD) (see U.S. Pat. No. 4,962,162, and Japanese Patent No. 2552413).

The fine solid carriers used in the invention include animal erythrocytes, gelatin particles, latex particles, magnetic particles, and the like. The gelatin particle referred to here indicates a particle composed of water soluble polysaccharides, sodium metaphosphate and an aldehyde crosslinking agent and the like in addition to gelatin (see JP 93-306113 A and JP 88-48021 B), the latex particle indicates a particle composed of a synthetic resin such as a polystyrene and acrylic resin which is an organic macromolecule, and is also commercially available. It is also possible to preferably use commercially available articles.

The fine solid carriers used in the invention include those processed to have magnetism as a magnetic particle whose core is an organic macromolecule and surface has a ferric oxide type ferrite coating layer. The magnetic particles can efficiently perform B/F separation utilizing magnetic force (see, Japanese Patents No. 3192149 and No. 2979414). In particular, the magnetic particles preferably used include, for example, particles where a core is magnetite and silane is coated (see JP 80-141670 A and JP 75-122997 A), particles where a core is a magnetic metal oxide and silane is coated (see JP 85-1564 A), magnetic particles where a core is an organic macromolecular compound, having a ferric oxide type ferrite coating layer (see Japanese Patent No. 2979414), and further particles having gelatin on a surface of magnetic particles where a core is an organic macromolecular compound (see Japanese Patent No. 3192149).

The fine solid carriers are not particularly limited thereto, and proper carriers are selected depending on a purpose of each measurement and a constitution of a kit used. So long as it is the carrier used in the solid phase immunoassay, the effects of the invention are exerted by the chemiluminescence enhancer.

The chemiluminescence enhancer according to the invention can be prepared by the treatment using the reagent having the oxidation or reduction property. An oxidizing agent or reducing agent used here includes ammonium persulfate, sodium periodate, sodium sulfite, sodium hypochlorite, hydrogen peroxide, sodium metaperiodate, potassium permanganate, potassium dichromate, and the like. The particularly preferable oxidizing agent or reducing agent can include ammonium persulfate, sodium sulfite, sodium hypochlorite, and sodium metaperiodate, and more preferably can include sodium sulfite and sodium hypochlorite.

When the chemiluminescence enhancer according to the invention is prepared, a chemiluminescence enhancer of the above general formula [I] or [II] manufactured by the known method or the chemiluminescence enhancer of a commercially available article is treated with the above oxidizing or reducing agent under an appropriate condition. As the treatment condition, by considering chemical species, molecular weight, concentration and the like of the chemiluminescence enhancer, it is possible to appropriately select the reagent concentration, the reaction time, the reaction temperature, the solvent system used and the like of the oxidizing agent or the reducing agent. The condition is not particularly limited, and for example, when the chemiluminescence enhancer is at an amount of about several g to some hundreds g, the chemiluminescence enhancer according to the invention can be obtained by the treatment with 5 mM sodium sulfite at room temperature for one hour, or 0.1% sodium hypochlorite at room temperature for two hours, or 1 mM ammonium persulfate and 1 mM sodium metaperiodate at 60° C. for two hours, or 15% hydrogen peroxide at room temperature for 17 hours, or 1 mM potassium permanganate and 1 mM potassium dichromate at 80° C. for two hours. It is known that sodium sulfite exhibits the oxidation property or the reduction property depending on the condition.

As exemplified in the following Examples, it is desirable that the chemiluminescence enhancer of the invention is purified using a dialysis membrane which cuts off ones with and less than the molecular weight of about 14,000 after the treatment with sodium hypochlorite. It has been shown that many of the untreated chemiluminescence enhancers can not pass through a 300,000 molecular weight cut-off ultrafiltration filter whereas the chemiluminescence enhancer of the invention can pass through it. Furthermore, it has been found that even in the chemiluminescence enhancer whose permeability through the filter is low depending on the condition of oxidation/reduction, the permeability of the chemiluminescence enhancer of the invention is enhanced by changing a condition of a dialysis solution.

As exemplified in the following Examples, it has been shown that when the chemiluminescence enhancer of the invention is added to the fine solid carriers, i.e., for example, a dispersion system of magnetic particles, dispersibility is improved, compared to the addition of the untreated chemiluminescence enhancer. It is believed that the favorable dispersibility of such fine solid carriers brings enhancement and stabilization of luminescence (signal) by the enzymatic reaction of the chemiluminescent substrate having dioxetane.

EXAMPLES

Hereinafter, the invention is concretely explained based on Examples. However, the invention is not limited to the following Examples.

Example 1-1

Effect of Untreated TBQ and Oxidized/Reduced TBQ on Chemiluminescence Measurement To 2 ml of TBQ solution (35.2 mg/ml), 2 ml of 2 mM sodium sulfite solution, 0.015% (effective chlorine concentration) sodium hypochlorite solution, 2 mM sodium metaperiodate or 2 mM ammonium persulfate was added, mixed, and subsequently treated at 60° C. for 4 hours. This treated TBQ was dispensed in a dialysis membrane (molecular weight cut-off, 12,000 to 14,000, supplied from Sanko Junyaku Co., Ltd.), and then dialyzed using MilliQ water (ultrapure water) as an external solution to make the treated TBQ. Next, 0.4 mg/ml AMPPD solution (0.2 M diethanolamine (DEA), 1 mM magnesium chloride ($MgCl_2$), 0.05% sodium azide ($NaN_3$), pH 10.0) containing 0.8 mg/ml untreated TBQ or treated TBQ was prepared (substrate solution). Magnetic particles (200 μl) binding 0.015% alkali phosphatase (ALP) was dispensed in a reaction vessel, and the particles were attracted to a magnet by putting the magnet close to the particles to eliminate a supernatant and wash. To this reaction vessel, 200 μl of the above substrate solution was added and mixed, reacted at 37° C. for 5 min, subsequently emission of light(signal) was counted by a photon counter (supplied from Hamamatsu Photonics K.K.), and an integrated value for 2 seconds was calculated. The reaction of the above magnetic particles with the substrate was performed five times. This result is shown in Table 1. Compared to the untreated TBQ, in the treated TBQ group, in all treatment conditions, the signal was increased and repeatability (CV value) was also enhanced.

TABLE 1

| | | Treated TBQ | | | |
|---|---|---|---|---|---|
| | Untreated TBQ | Na sulfite | Na hypochlorite | Na metaperiodate | Ammonium persulfate |
| Count | 1188601 | 1795546 | 1900953 | 1882699 | 1887294 |
| | 1144091 | 1803082 | 1893218 | 1880734 | 1853619 |
| | 1159564 | 1760605 | 1859213 | 1864943 | 1855904 |
| | 1100897 | 1774889 | 1881518 | 1859709 | 1852409 |
| | 1164963 | 1768074 | 1864585 | 1845497 | 1837743 |
| Average | 1151623 | 1780439 | 1879897 | 1866716 | 1857394 |
| CV | 2.8% | 1.0% | 1.0% | 0.8% | 1.0% |

Example 1-2

Effect of Untreated TBQ and Oxidized/Reduced TBQ on Particle Dispersion

DEA solution (0.1 M, pH 10.0) containing 0.8 mg/ml untreated TBQ or treated TBQ was prepared. Then, 100 μl of 0.03% magnetic particles were dispensed in a reaction vessel, and the particles were attracted to a magnet by putting the magnet close to the particles and the supernatant was eliminated. The DEA solution (200 μl) including the above TBQ was added and stirred for 30 seconds. Fifteen seconds after stirring, 150 μl was taken from a solution surface by a Pipetman (supplied from Gilson, a micropipette), dispensed in a cell for a spectrophotometer, and after 10 seconds, a turbidity (OD500) was measured by the spectrophotometer (UV-1200, supplied from Shimadzu Corporation). This result is shown in Table 2. Compared to the untreated TBQ, in the treated TBQ group, the turbidity was higher and the dispersion of particles was enhanced.

TABLE 2

|  | Untreated TBQ | Treated TBQ | | | |
|---|---|---|---|---|---|
|  |  | Na sulfite | Na hypo-chlorite | Na metaperiodate | Ammonium persulfate |
| Turbidity | 0.035 | 0.261 | 0.368 | 0.430 | 0.487 |

Example 2-1

Effect of Untreated TBQ and Oxidized/Reduced TBQ on Chemiluminescence Measurement To 2 ml of 35.2 mg/ml TBQ solution, 2 ml of a solution including 0.005%, 0.05%, or 0.5% sodium hypochlorite as an effective chlorine concentration was added, mixed, and subsequently left at 25° C. for 24 hours. Next, a mixture is dispensed in a dialysis membrane (molecular weight cut-off, 12,000 to 14,000 supplied from Sanko Junyaku Co., Ltd.), and subsequently the dialysis using MilliQ water as an external solution was performed to make the treated TBQ. Then, 0.2 mg/ml AMPPD solution (0.1 M DEA, 1 mM $MgCl_2$, 0.05% $NaN_3$, pH 10.0) containing 0.8 mg/ml untreated TBQ or treated TBQ was prepared (substrate solution). Next, 200 μl of 0.015% ALP-binding magnetic particles were dispensed in a reaction vessel, and the particles were attracted to a magnet by putting the magnet close to the particles, and the supernatant was eliminate and washed. Then, 200 μl of the above substrate solution was added and mixed, reacted at 37° C. for 5 min, subsequently emission of light (signal) was counted by a photon counter (supplied from Hamamatsu Photonics K.K.), and an integrated value for 2 seconds was calculated. This result is shown in Table 3. Compared to the untreated TBQ, in the treated TBQ group, in all treatment conditions, the signal was increased and repeatability (CV value) was also enhanced.

TABLE 3

|  |  | TBQ treated with sodium hypochlorite | | |
|---|---|---|---|---|
|  | Untreated TBQ | 0.005% treatment | 0.05% treatment | 0.5% treatment |
| Count | 1243067 | 1939907 | 1874673 | 1742837 |
|  | 1138533 | 1951098 | 1904467 | 1747014 |
|  | 1185676 | 1958058 | 1896528 | 1742927 |
|  | 1213137 | 1958925 | 1928099 | 1749573 |
|  | 1046363 | 1944462 | 1889804 | 1753686 |
|  | 1198577 | 1931453 | 1879883 | 1738024 |
| Average | 1170892 | 1947317 | 1895576 | 1745677 |
| CV | 6.0% | 0.6% | 1.0% | 0.3% |

Example 2-2

Effect of Untreated TBQ and Oxidized/Reduced TBQ on Particle Dispersion

A treated TBQ was obtained by the method described in Example 2-1. A DEA solution (0.1 M, pH 10.0) containing 0.8 mg/ml untreated TBQ or treated TBQ was prepared. Then, 100 μl of 0.03% magnetic particles were dispensed in a reaction vessel, and the particles were attracted to a magnet by putting the magnet close to the particles and the supernatant was eliminated. The DEA solution (200 μl) including the TBQ was added and stirred for 30 seconds. Fifteen seconds after stirring, 150 μl was taken from a solution surface by a Pipetman (supplied from Gilson, a micropipette), dispensed in a cell for a spectrophotometer, and after 10 seconds, a turbidity (OD500) was measured by the spectrophotometer (UV-1200, supplied from Shimadzu Corporation). This result is shown in Table 4. Compared to the untreated TBQ, in the treated TBQ group, the turbidity was higher and the dispersion of particles was enhanced.

TABLE 4

|  |  | TBQ treated with sodium hypochlorite | | |
|---|---|---|---|---|
|  | Untreated TBQ | 0.005% treatment | 0.05% treatment | 0.5% treatment |
| Turbidity | 0.035 | 0.314 | 0.385 | 0.510 |

Example 3

Ultrafiltration Filter Permeability of Untreated TBQ and Oxidized/Reduced TBQ

The untreated TBQ and the treated TBQ were diluted to 1 mg/ml or less with 0.1 M or 1 M sodium chloride (NaCl). This solution was ultrafiltrated through a 300,000 molecular weight cut-off ultrafiltration filter (supplied from Millipore), an absorbance (OD268) of a filtrate was measured, and a permeability was calculated. The result is shown in Table 5. Compared to the untreated TBQ, the filter permeability of the treated TBQ was increased. For TBQ treated with 0.005% sodium hypochlorite whose permeability was low in 0.1 M NaCl solution, when dissolved in 1 M NaCl solution, its filter permeability was enhanced.

TABLE 5

|  |  | Un-treated TBQ | TBQ treated with sodium hypochlorite | | |
|---|---|---|---|---|---|
|  |  |  | 0.005% treatment | 0.05% treatment | 0.5% treatment |
| Filter permeability | 0.1 M NaCl solution | 3% | 31% | 94% | 95% |
|  | 1 M NaCl solution | 7% | 96% |  |  |

Example 4

Effect of Untreated TBQ and Oxidized/Reduced TBQ on Chemiluminescence Immunoassay (1)

To 2 ml of 35.2 mg/ml TBQ, 2 ml of 2 M sodium sulfite solution was added, mixed, and then treated at 60° C. for 4 hours. Next, this was dispensed in a dialysis membrane (molecular weight cut-off, 12,000 to 14,000, supplied from Sanko Junyaku Co., Ltd.), and the dialysis was performed using MilliQ water as an external solution to make the treated TBQ. Next, 0.02 mg/ml AMPPD solution (0.1 M DEA, 1 mM $MgCl_2$, 0.05% $NaN_3$, pH 10.0) containing 0.8 mg/ml untreated TBQ or treated TBQ was prepared (substrate solution). Test samples containing 0, 10, 100, 800 and 2000 ng/ml of α fetoprotein (AFP) were diluted to 20 times with a BSA solution. Each measurement sample (20 μl) was added into a reaction vessel in which 50 μl of 0.03% anti-AFP antibody-binding magnetic particles were placed, mixed, and reacted at 37° C. for 8 min. Subsequently, the particles were attracted to a magnet by putting the magnet close to the reaction vessel to eliminate a supernatant and wash. Then, 50 μl of 0.1 μg/ml ALP-conjugating anti-AFP antibody solution was added, mixed, and reacted at 37° C. for 8 min. After the reaction, the particles were attracted to a magnet by putting the magnet close to the reaction vessel, the supernatant was eliminated and washed. The above substrate solution (200 μl) was added to these particles, mixed, and reacted at 37° C. for 4 min. Subsequently, emission of light (signal) was counted by a photon counter (supplied from Hamamatsu Photonics K.K.), and an integrated value for two seconds was calculated. The result is shown in Table 6. Compared to the cases of the untreated TBQ, repeatability (CV value) using the TBQ treated with sodium sulfite was enhanced.

[Table 6]

TABLE 6

| | | AFP concentration (ng/ml) | | | |
|---|---|---|---|---|---|
| | 0 | 10 | 100 | 800 | 2000 |
| | | Untreated TBQ | | | |
| Count | 737 | 22413 | 190157 | 1204985 | 2201469 |
| | 689 | 25275 | 205970 | 874704 | 1396455 |
| | 822 | 30756 | 199645 | 932275 | 2335765 |
| | 824 | 30605 | 205809 | 816211 | 2214843 |
| | 859 | 33443 | 189985 | 946657 | 1430978 |
| | 853 | 22297 | 196053 | 1064297 | 1374801 |
| Average | 797 | 27465 | 197937 | 973188 | 1825719 |
| CV | 8.6% | 17.3% | 3.6% | 14.4% | 25.6% |
| | | TBQ treated with sodium sulfite | | | |
| Count | 354 | 17298 | 165651 | 1230392 | 2391362 |
| | 380 | 17595 | 166482 | 1236687 | 2514891 |
| | 370 | 17634 | 167006 | 1245664 | 2397218 |
| | 385 | 17515 | 167636 | 1192276 | 2515427 |
| | 381 | 17557 | 166714 | 1191075 | 2442702 |
| | 371 | 16806 | 164900 | 1216407 | 2540877 |
| Average | 374 | 17401 | 166398 | 1218750 | 2467080 |
| CV | 3.0% | 1.8% | 0.6% | 1.9% | 2.6% |

Example 5

Effect of Untreated TBQ and Oxidized/Reduced TBQ on Chemiluminescence Immunoassay (2)

To 300 ml of 35.2 mg/ml TBQ solution, 15 ml of 1 M sodium sulfite-HCl solution (pH 6.0) was added, mixed and reacted at 25° C. for 24 hours. Next, this was dispensed in a dialysis membrane (molecular weight cut-off, 12,000 to 14,000, supplied from Sanko Junyaku Co., Ltd.), and the dialysis was performed using MilliQ water as an external solution to make the treated TBQ. Next, 0.2 mg/ml AMPPD solution (0.1 M DEA, 1 mM MgCl$_2$, 0.05% NaN$_3$, pH 10.0) containing 0.8 mg/ml untreated TBQ or treated TBQ was prepared (substrate solution). As with the above Example 4, using α-fetoprotein as a test sample, an immunoassay was performed, and chemiluminescence (signal) was counted to perform a measurement. The result is shown in Table 7. Compared to the cases of the untreated TBQ, repeatability (CV value) using the TBQ treated with sodium sulfite was enhanced.

TABLE 7

| | | AFP concentration (ng/ml) | | | |
|---|---|---|---|---|---|
| | 0 | 10 | 100 | 800 | 2000 |
| | | Untreated TBQ | | | |
| Count | 549 | 37542 | 188792 | 1064676 | 1714369 |
| | 560 | 38510 | 219614 | 908606 | 1985371 |
| | 609 | 41285 | 212975 | 958981 | 1866508 |
| | 551 | 38169 | 207767 | 1051242 | 1464529 |
| | 505 | 41844 | 232717 | 983756 | 1498278 |
| | 472 | 27779 | 211984 | 1054501 | 1684947 |
| Average | 541 | 37522 | 212308 | 1003627 | 1702334 |
| CV | 8.8% | 13.5% | 6.8% | 6.3% | 11.9% |
| | | TBQ treated with sodium sulfite | | | |
| Count | 374 | 27079 | 234281 | 1140508 | 2163595 |
| | 380 | 25361 | 233081 | 1160725 | 1925163 |
| | 362 | 27141 | 220616 | 1153611 | 2031717 |
| | 363 | 25705 | 228368 | 1117495 | 2060136 |
| | 426 | 27389 | 221167 | 1104866 | 1978776 |
| | 399 | 24851 | 227564 | 1130180 | 2036848 |
| Average | 384 | 26254 | 227513 | 1134564 | 2032706 |
| CV | 6.4% | 4.1% | 2.5% | 1.9% | 4.0% |

Example 6

Effect of Untreated BDMQ and Oxidized/Reduced BDMQ on Chemiluminescence Immunoassay To 10 ml of BDMQ solution (25.4 mg/ml), 0.5 ml of 1 M sodium sulfite-HCl solution (pH 6.0) was added, mixed and reacted at 25° C. for 24 hours. Next, this was dispensed in a dialysis membrane (molecular weight cut-off, 12,000 to 14,000, supplied from Sanko Junyaku Co., Ltd.), and the dialysis was performed using MilliQ water as an external solution to make a treated BDMQ.

Next, 0.2 mg/ml AMPPD solution [0.1 M diethanolamine (DEA), 1 mM magnesium chloride (MgCl$_2$), 0.05% sodium azide (NaN$_3$), pH 10.0] containing 0.4 mg/ml untreated BDMQ or treated BDMQ was prepared (substrate solution).

Test samples containing 0, 10, 100, 800 and 2000 ng/ml of α fetoprotein (AFP) were diluted to 10 times with a BSA solution. Each measurement sample (20 μl) was added into a reaction vessel in which 250 μl of 0.015% anti-AFP antibody-binding magnetic particles were placed, mixed, and reacted at 37° C. for 10 min. Subsequently, the particles were attracted to a magnet by putting the magnet close to the reaction vessel to eliminate a supernatant and wash. Then, 250 μl of 0.1 μg/ml ALP-conjugating anti-AFP antibody was added, mixed, and reacted at 37° C. for 10 min. After the reaction, the particles were attracted to a magnet by putting the magnet close to the reaction vessel, the supernatant was eliminated and washed. The above substrate solution (200 μl) was added to these particles, mixed, and reacted at 37° C. for 5 min. Subsequently, chemiluminescence (signal) was counted by a photon counter (supplied from Hamamatsu Photonics K.K.), and an integrated value for two seconds was calculated. The result is shown in Table 8. Compared to the cases of the untreated BDMQ, repeatability (CV value) using the BDMQ treated with sodium sulfite was enhanced.

TABLE 8

| | AFP concentration (ng/ml) | | | | |
|---|---|---|---|---|---|
| | 0 | 10 | 100 | 800 | 2000 |
| | Untreated BDMQ | | | | |
| Count | 235 | 29915 | 200489 | 860407 | 1600060 |
| | 242 | 30126 | 203080 | 904037 | 1735060 |
| | 222 | 29949 | 198255 | 891405 | 1759976 |
| | 242 | 29466 | 208122 | 935003 | 1512594 |
| Average | 235 | 29864 | 202487 | 897713 | 1651923 |
| CV | 4.00% | 0.90% | 2.10% | 3.40% | 7.10% |
| | BDMQ treated with sodium sulfite | | | | |
| Count | 201 | 24969 | 198765 | 1212549 | 2354980 |
| | 212 | 25586 | 195978 | 1210283 | 2371754 |
| | 207 | 25043 | 196434 | 1213840 | 2339963 |
| | 184 | 25086 | 195111 | 1219413 | 2371016 |
| Average | 201 | 29864 | 202487 | 897713 | 1651923 |
| CV | 6.10% | 0.90% | 0.80% | 0.40% | 0.90% |

Example 7

Effects of Untreated BDMQ and Oxidized/Reduced BDMQ on Particle Dispersion

To 10 ml of BDMQ solution (25.4 mg/ml), 0.5 ml of 1 M sodium sulfite-HCl solution (pH 6.0) was added, mixed and reacted at 25° C. for 24 hours. Next, this was dispensed in a dialysis membrane (molecular weight cut-off, 12,000 to 14,000, supplied from Sanko Junyaku Co., Ltd.), and the dialysis was performed using MilliQ water as an external solution to make the treated BDMQ.

Next, 0.1 M DEA (pH 10.0) containing 0.4 mg/ml untreated BDMQ or treated BDMQ was prepared. Then, 100 μl of 0.03% magnetic particles were dispensed to a reaction vessel, and the particles were attracted to a magnet by putting the magnet close to the particles, and the supernatant was eliminated. The DEA solution (200 μl) including the above BDMQ was added and stirred for 30 seconds. Fifteen seconds after stirring, 150 μl was taken from a solution surface by a Pipetman (supplied from Gilson, a micropipette), dispensed in a cell for a spectrophotometer, and after 10 seconds, a turbidity (OD500) was measured by the spectrophotometer (UV-1200, supplied from Shimadzu Corporation. This result is shown in Table 9. Compared to the untreated BDMQ, in the treated BDMQ group, the turbidity was higher and the dispersion of particles was enhanced.

TABLE 9

| | Untreated BDMQ | Treated BDMQ |
|---|---|---|
| Turbidity | 0.045 | 0.339 |

EFFECTS OF THE INVENTION

As in the above, by treating with the oxidizing agent or the reducing agent, the chemiluminescence enhancer has been provided, which is used for the signal detection in the solid immunoassay using the antigen or/and the antibody immobilized onto fine solid carriers dispersible in the liquid medium, improves the dispersibility of the fine solid carriers compared to conventional chemiluminescence enhancers, and is excellent in enhancement of chemiluminescence by the enzymatic reaction of the chemiluminescent substrate having dioxetane. Also, the chemiluminescence method and the kit using the chemiluminescence enhancer have been provided. When using the chemiluminescence enhancer of the invention, the within-run reproducibility of the measurement values is enhanced and more precise quantification becomes possible.

The invention claimed is:

1. A method of producing chemiluminescence in a solid phase immunoassay, comprising:
   contacting at least one antigen or/and an antibody immobilized onto fine solid carriers dispersed in a liquid medium with a chemiluminescent substrate comprising:
   at least one dioxetane,
   an enzyme for performing chemiluminescence, and
   at least one isolated pretreated chemiluminescence enhancer selected from the group consisting of a water soluble quaternary ammonium salt, a water soluble sulfonium salt and a water soluble quaternary phosphonium salt, each of which has been pretreated with an oxidizing agent or a reducing agent and then isolated from the oxidizing or reducing agent, wherein said isolated pretreated chemiluminescence enhancer enhances the emission of light caused by the reaction of said chemiluminescent substrate with the said enzyme.

2. The method according to claim 1, wherein the chemiluminescence enhancer does not substantially comprise a component with a molecular weight of more than 400,000 daltons in molecular weight as separated by an ultrafiltration method.

3. The method according to claim 1, wherein the chemiluminescent substrate comprises at least one dioxetane represented by general formula:

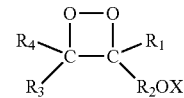

wherein $R_2$ is an aryl group substituted with an X-oxy group, which forms 1,2-dioxetane compound which is an unstable oxide intermediate when X is eliminated by activator enzyme to induce a reaction, which unstable 1,2-dioxetane compound is decomposed with releasing electron energy to produce light and two carbonyl-containing compounds of general formulae,

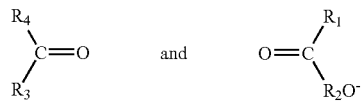

and X is a chemically easily reactive group which is eliminated by an enzyme;

$R_1$ is one selected from the group consisting of an alkyl group, an alkoxy group, an aryloxy group, a dialkylamino group, a trialkylsilyloxy group, an arylsilyloxy group, an aryl group and an aryl group which is bound to an aryl group $R_2$ to form a polycyclic aryl group with X-oxy group substitution, which spiro-binds to a 1,2-dioxetane ring;

$R_3$ and $R_4$ are each an alkyl group or a heteroalkyl group, or $R_3$ and $R_4$ may be together bound to form a polycyclic alkylene group which spiro-binds to the 1,2-dioxetane ring.

4. The method according to claim 1, wherein the chemiluminescence enhancer is prepared from a monomer selected from the group consisting of a quaternary ammonium salt, a sulfonium salt, a quaternary phosphonium salt, and mixtures thereof.

5. The method according to claim 1, wherein the chemiluminescence enhancer is a polymerized quaternary ammonium salt, a polymerized sulfonium salt, a polymerized quaternary phosphonium salt, or copolymers thereof.

6. The method according to claim 1, wherein the chemiluminescence enhancer is selected from the group consisting of poly[vinylbenzyl(benzylmethyl ammonium chloride)], poly(vinylbenzyltrimethyl ammonium chloride), poly[vinylbenzyl(tributyl ammonium chloride)], benzylmethylcetyl ammonium chloride, polymethacrylamidepropylenemethyl ammonium chloride, poly[vinylbenzyl(triethyl ammonium chloride)], poly[vinylbenzyl(2-benzylamino)ethyldimethyl ammonium chloride], poly[vinylbenzyldimethyl(2-hydroxy)ethyl ammonium chloride], poly[vinylbenzyl(trimethylphosphonium chloride)], poly[vinylbenzyl(tributylphosphonium chloride and poly[vinylbenzyl(trioctylphosphonium chloride)] and copolymers thereof.

7. The method according to claim 1, wherein the solid carrier is a particle.

8. The method according to claim 7, wherein the particle is a magnetic particle.

9. The method according to claim 1, wherein the chemiluminescence enhancer has been treated with at least one oxidizing agent or a reducing agent selected from the group consisting of ammonium persulfate, sodium sulfite, sodium hypochlorite, hydrogen peroxide, sodium metaperiodate, potassium permanganate and potassium dichromate.

10. The method according to claim 1, wherein the enzyme is at least one of acid phosphatase, alkali phosphatase, glucosidase, glucuronidase or esterase.

11. The method according to claim 9, wherein the chemiluminescence enhancer has been treated with at least one oxidizing agent or a reducing agent selected from the group consisting of sodium hypochlorite and sodium metaperiodate.

* * * * *